United States Patent [19]

Koyano et al.

[11] Patent Number: 4,463,763

[45] Date of Patent: Aug. 7, 1984

[54] ULTRASONIC COMPOUND SCANNING DIAGNOSTIC APPARATUS

[75] Inventors: Akira Koyano; Seiichiro Mizuno, both of Mitaka, Japan

[73] Assignee: Aloka Co., Ltd., Tokyo, Japan

[21] Appl. No.: 302,802

[22] Filed: Sep. 16, 1981

[30] Foreign Application Priority Data

Sep. 16, 1980 [JP] Japan .............................. 55-127301

[51] Int. Cl.$^3$ ............................................. A61B 10/00
[52] U.S. Cl. .................................................. 128/661
[58] Field of Search ....................... 178/660, 661, 663; 73/618-620, 625-626

[56] References Cited

U.S. PATENT DOCUMENTS

| | | | |
|---|---|---|---|
| 4,159,462 | 6/1979 | Rocha et al. .................... | 128/661 X |
| 4,209,022 | 6/1980 | Dory ................................. | 128/660 |
| 4,372,323 | 2/1983 | Takemura et al. ............... | 73/625 X |
| 4,381,787 | 5/1983 | Hottinger ........................ | 128/660 |

OTHER PUBLICATIONS

Takemura, Y. et al., "High Speed UTS–Cardiotomograph Sonolayergraph Model SSL-51H", Toshiba Review #98, pp. 25-30, Jul.-Aug., 1975.
Carpenter, D. A. et al., "A Multi-Mode Real Time Scanner", UTS in Med. & Biol., vol. 6, No. 3, pp. 279-284, (1980).
Holmes, N. G. et al., "Adoptive Gamma Camera Gating", Jrnl. Med. Eng. & Tech. (G.B.), vol. 2, No. 1, Jan. 1978, pp. 13-16.
Ito, K. et al., "Realtime Display Achieves 3D UTS Diagnoses", JEE, Nov. '79, vol. 16, No. 155, pp. 64-69.
Ito, K. et al., "Realtime Slow Motion Display", JEEE, Sep. 1980, vol. 17, No. 165, pp. 78-81.
Japan Electronic Engineering, "A Real-Time UTS Diagnostic System for Dynamic & Still Images", Dec. 1977, JEE, No. 132, pp. 20-26.

Primary Examiner—Kyle L. Howell
Assistant Examiner—Francis J. Jaworski
Attorney, Agent, or Firm—Koda and Androlia

[57] ABSTRACT

An ultrasonic diagnostic apparatus including a compound scanner, a transmitting and receiving control circuit, a digital scanning convertor, a display section, a mode change-over switch, a position signal generator and a heart beat synchronizing signal generator, whereby operation of the change-over switch makes it possible to display dynamic picture images or still picture images at selected time phases by real-time sector scanning and compound sector scanning.

5 Claims, 7 Drawing Figures

| | DISPLAY MODE | PICTURE IMAGE POSITION DURING DISPLAY | PICTURE IMAGE DATA |
|---|---|---|---|
| REAL TIME SECTOR SCANNING | I — DYNAMIC PICTURE IMAGE DISPLAY | FIXED | ALWAYS UPDATED |
| | II — STATIC PICTURE IMAGE DISPLAY | FIXED | NOT UPDATED |
| COMPOUND SECTOR SCANNING | III — COMPOUND PICTURE IMAGE DISPLAY | MOVING IN ACCORDANCE WITH ARM ACTION | KEPT ON STORED |
| | IV — HEART BEAT SYNCHRONIZING PICTURE IMAGE DISPLAY | — DITTO — | — DITTO — |
| | V — UCG MODE | AS CONVENTIONAL | AS CONVENTIONAL |

ULTRASONIC COMPOUND SCANNING DIAGNOSTIC APPARATUS

BACKGROUND OF THE INVENTION

1. Field of the Invention

The present invention relates to a ultrasonic diagnostic apparatus, and more particularly to a ultrasonic diagnostic apparatus in which is performed electronic sector scanning of the ultrasonic transducers and mechanical compound scanning of the ultrasonic transducers along a selected body surface over the organs to be diagnosed and the combination of the above mentioned two scanning methods can easily select a picture image by selected display modes.

2. Description of The Prior Art

In FIG. 1 is shown a block diagram of a conventional electronic sector scanning ultrasonic diagnostic apparatus. In this prior art device an electronic sector scanning probe 10 in which a plurality of ultrasonic transducers are arranged at equal distances from each other transmits and receives ultrasonic beams to and from a body to be examined by means of sector scanning.

In order to control transmitting and receiving actions a transmitting-receiving control circuit is prepared. The transmitting-receiving control circuit 12 includes a repeating pulse generator 14 producing repeating pulses which are supplied to a transmitter-receiver 18 by way of an ultrasonic transducer control signal generator 16. The transmitter-receiver 18 supplies driving signals having a predetermined delay time to the selected transducer of the probe 10 to control the transmitting and receiving actions of the probe 10. The above mentioned driven ultrasonic transducer group is controlled to work one after another at every repeating cycle to perform well-known electronic scanning action. After the signals received by the transmitter-receiver 18 are detected by a detector 20, the signals are converted into echo signals having luminance in accordance with the strength of received echo by a luminance modulation voltage generator 22. The output from the transmitting-receiving control circuit one provided to a digital scanning convertor 24.

The digital scanning convertor 24 memorizes and stores the echo signals, and further, includes frame memory and signal convertor to perform requested signal conversion. The digital scanning convertor 24 also receives input synchronized signals from the repeating pulse generator 14. The output from the convertor 24 is supplied to a display section 26 composed of a standard television picture screen, etc. to display real-time dynamic picture images by sector scanning so that examiners can be provided with required diagnostic information.

In the prior art device shown in FIG. 1, as described heretofore, sector scanning images of the portion to be examined can be displayed in real-time, but a wider area of the body to be examined cannot be observed at the same time.

In the prior art device, it is possible to continuously display the sector scanning picture images of wider area by the scanning of the probe in manual operation or the like along the elected body surface over the organs to be diagnosed. Since, in this case the sector picture image is displayed at a fixed position on the picture display screen, and the actual probe position cannot be informed in the display area, and further, the examiner must always consider the relation between the displayed picture image and the position of the probe 10 in the diagnostic area, it is difficult to diagnose with accuracy and mistaken diagnosis can result.

As described hereinabove, in the prior art device, the electronic sector scanning and the compound scanning cannot be combined, and the real-time picture image updating cannot be halted at a selected time phase. In other words, still picture images of moving organs at predetermined time phases, sytole or diastole for example, cannot be recorded for diagnosis from a plurality of different position over the body surface and displayed as one picture image by means of overlapping such images.

SUMMARY OF THE INVENTION

Accordingly, it is a general object of the present invention to provide a ultrasonic diagnostic apparatus in which the electronic sector scanning and the compound scanning can be combined and picture images having selected display modes can be easily obtained by the selected control of the memory storage and signal conversion of the echo signals supplied by the combination of two scanning methods.

In keeping with the principles of the present invention, the object is accomplished by an ultrasonic diagnostic apparatus including an electronic sector scanning probe in which a plurality of ultrasonic transducers are arranged at equal distance, a compound scanner holding the probe to perform free compound scanning along a selected body surface over the organs to be diagnosed and being attached to rotary encoders to detect compound scanning positions, a transmitting-receiving control circuit which electronically scans the probe and transmits and receives sector scanning ultrasonic beams to and from a body to be examined, a digital scanning convertor which memorizes and stores the echo signals obtained from the transmitting-receiving control circuit and performs the selected signal converting process, a display section which displays picture images in accordance with picture image signals output from the digital scanning convertor, a mode change-over switch which is connected to the digital scanning convertor and switches to select a selected display mode by controlling memory storage and signal conversion of the echo signals in the convertor, a position signal generator which outputs picture image display position signals to the mode change-over switch in accordance with compound scanning position detecting signals obtained from the rotary encoders of the compound scanner, and a heart beat synchronizing signal generator which outputs heart beat synchronizing signals to the mode change-over switch in accordance with heart beat signals, whereby operation of the change-over switch makes it possible to display dynamic picture images or still picture images at selected time phases by real-time sector scanning and compound sector scanning.

BRIEF DESCRIPTION OF THE DRAWINGS

The above mentioned, other features and the object of the present invention will become more apparent by reference to the following description taken in conjunction with the accompanying drawings, wherein like referenced numerals denote like elements in which:

FIG. 5 is an illustration describing each of the display modes in accordance with the teachings of the present invention;

DESCRIPTION OF THE PREFERRED EMBODIMENT

Figure 1:
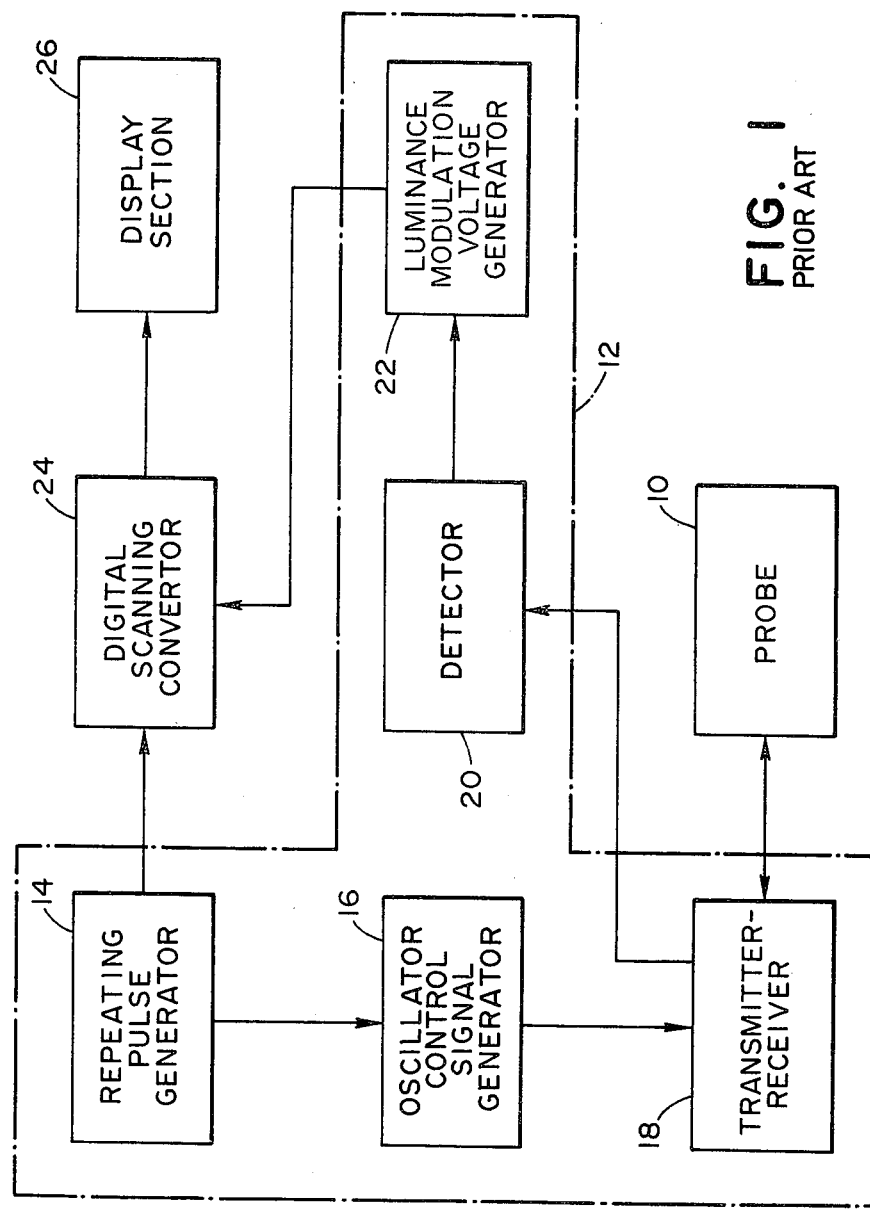
FIG. 1 is a block diagram showing one example of ultrasonic diagnostic apparatus in the prior art.
Figure 2:
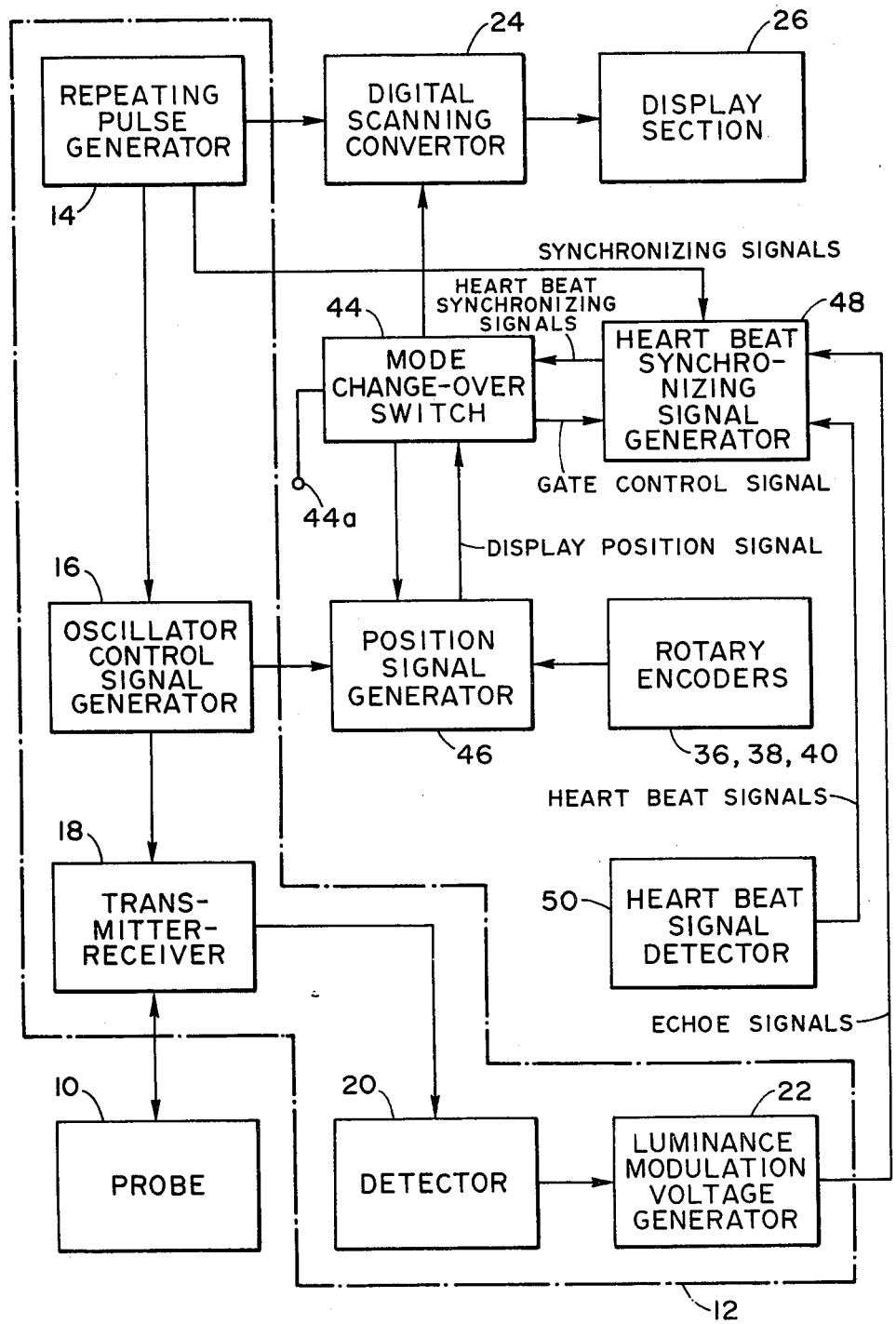
FIG. 2 is a block diagram showing a preferred embodiment of the ultrasonic diagnostic apparatus in accordance with the teachings of the present invention.

Referring more particularly to the drawings, shown in FIG. 2 is a block diagram of a preferred embodiment of ultrasonic diagnostic apparatus in accordance with the teachings of the present invention. The like elements in FIG. 1 are denoted by like numbers and their description will be omitted.

Figure 3:
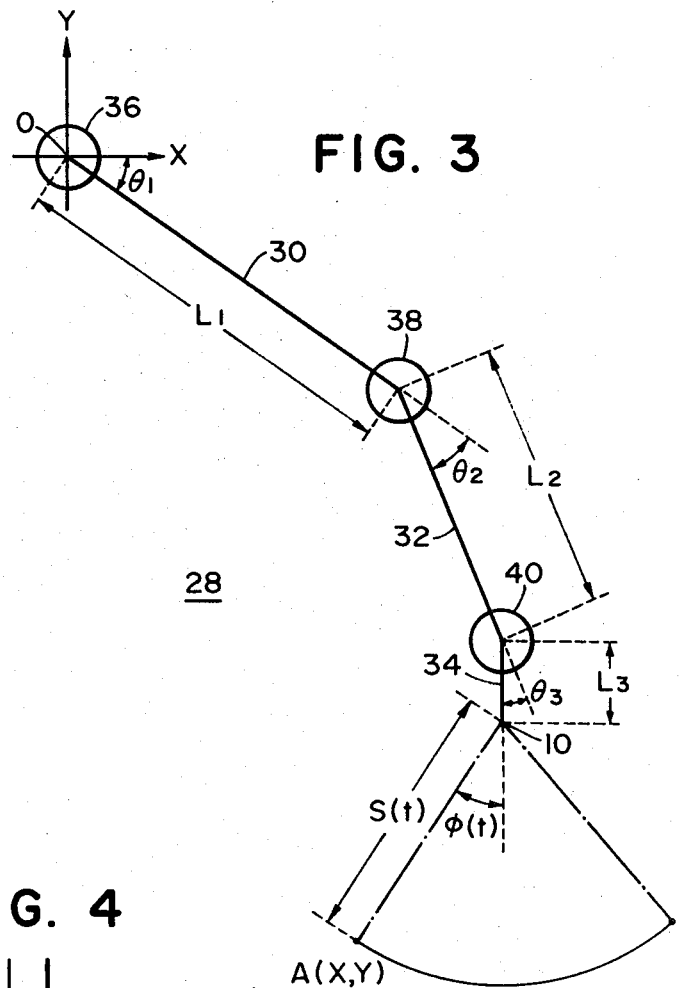
FIG. 3 is an illustration showing composition of a compound scanner in accordance with the teachings of the present invention.

An electronic sector scanning probe 10 according to the present invention is attached to the end of a compound scanner 28 illustrated in FIG. 3, and held to be freely scanned along a requested body surfce over the organs to be diagnosed. The compound scanner 28 includes three arms 30, 32 and 34 which are rotatably connected and combined one by one from the basic point O, and the probe 10 is fixed at the end of the arm 34. Each of the arm 30, 32 and 34 is rotatably controlled at their respective supporting axis so that the probe 10 can be freely scanned along the selected body surface over the organs to be diagnosed. Each rotatable support of the arms 30, 32 and 34 is attached to each of the rotary encoders 36, 38 and 40 so that amount of a rotation of the arms 30, 32 and 34 can be outputted as compound scanning position signals. Each length of the arms 30, 32 and 34 is chosen by predetermined values $L_1$, $L_2$ and $L_3$ and each rotated angle of the arms can be respectively obtained as $\theta_1$, $\theta_2$ and $\theta_3$ by each output of the rotary encoders 36, 38 and 40. Since a sector scanning beam position of the probe fixed at the end of compound scanner 28 is obtained by length S(t) and sector angle $\phi(t)$ which are respectively shown as function of time, the sector scanning beam position A(X and Y) is obtained on X and Y coordinates at the basic point shown in FIG. 3 by the following equation:

$$X = L_1 \cos \theta_1 + L_2 \cos(\theta_1 + \theta_2) + L_3 \cos(\theta_1 + \theta_2 + \theta_3) + S(t) \cos\{\theta_1 + \theta_2 + \theta_3 + \phi(t)\}$$

$$Y = L_1 \sin \theta_1 + L_2 \sin(\theta_1 + \theta_2) + L_3 \sin(\theta_1 + \theta_2 + \theta_3) + S(t) \sin\{\theta_1 + \theta_2 + \theta_3 + \phi(t)\}$$

Figure 4:
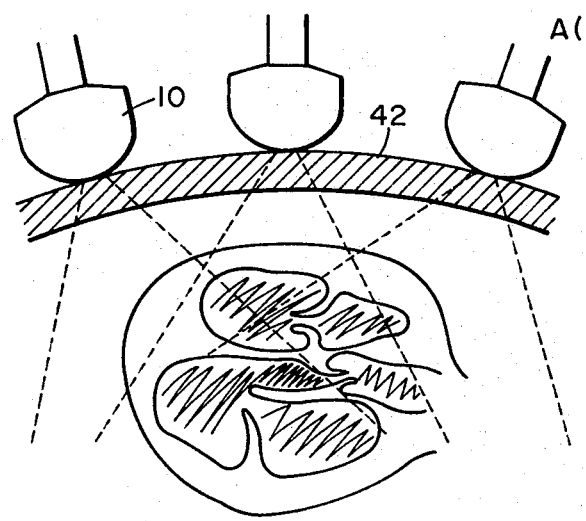
FIG. 4 is an illustration describing a scanning state of ultrasonic beams in accordance with the teachings of the present invention.

As described in the above, according to the present invention, not only performed is the electronic sector scanning of the probe 10, but also performed is manual or mechanical compound scanning of the probe 10. In FIG. 4 shown therein is one example of ultrasonic beams irradiated from the probe 10 to a body 42 to be examined in accordance with combination of the electronic sector scanning and the compound scanning.

In FIG. 2, in order to switch over and to choose a requested display mode by means of controlling memory storage of echo signals and signal converting action in a digital scanning convertor 24, the present invention is characterized in that a mode change-over switch 44 is provided and control signals are supplied from the mode change-over switch 44 to the digital scanning convertor 24. To the control panel of the mode change-over switch 44 supplied can be selected operation signals from a terminal 44a by an examiner, and supplied can be signals in accordance with respectively chosen display modes from respective signal generators, description of which will be made in the following.

The mode change-over switch 44 in this embodiment can select a mode displaying dynamic picture images for both of the real-time sector scanning and the compound sector scanning or still picture images at selected time phases, and also can select a well-known UCG display mode. Specification of the modes mentioned above to the control panel of the mode change-over switch 44 supplies requested control signals from the mode change-over switch 44 to the digital scanning converter 24.

The signal generators for the mode change-over switch 44 in the present invention include a position signal generator 46 and a heart beat synchronizing signal generator 48.

The position signal generator 46 outputs picture image position signals to the mode change-over switch 44 in accordance with compound scanning position detecting signals being obtained from the rotary encoders 36, 38 and 40 of the compound scanner 28 described hereinabove, and the transmitting and receiving order signals obtained from the above mentioned transducer control signal generator 16, and further, supplies the coordinate values (X, Y) also described hereinabove to the mode change-over switch 44 so that the picture images displayed on the screen in the display section 26 can be moved along the body surface over the organs to be diagnosed.

From the above described heart beat synchronizing signal generator 48 supplied can be heart beat synchronizing signals at a predetermined time phase in case of heart diagnosis to the mode change-over switch 44. For example, it is preferable to select systole or diastole as the above mentioned predetermined period. The heart beat synchronizing signal generator 48 in the embodiment is composed of gate circuit which opens the gate only at a time phase of the selected systole or diastole, and supplies echo signals output from a luminance modulation voltage generator 22 to the digital scanning converter 24 by way of the mode change-over switch 44. In order to do this action, a heart beat signal detector 50 is connected to the heart beat synchronizing signal generator 48, and heart beat signals of R waves, etc. obtained through an electrocardiograph can be utilized as a standard for heart beat synchronizing signals. Furthermore, to the heart beat synchronizing signal generator 48 supplied are repeating pulses outputted from the repeating pulse generator 14 and outputted are synchronizing signals per one frame sector scanning.

The preferred embodiment of the present invention is composed as described in the above, and its action will be hereinafter described in reference to display modes illustrated in FIG. 5.

A I display mode in FIG. 5 is the mode which displays dynamic picture images while the realtime sector scanning is being performed, and the same picture image display with the prior art device shown in FIG. 1 can be done. In other words, in the I display mode the mode change-over switch 44 makes the position signals invalid from the position signal generator 46, and supplies signals to the heart beat synchronizing generator 48 such that its gate is always kept open. Accordingly, the echo signals from the luminance modulation voltage generator 22 is provided to the digital scanning convertor 24 through the mode change-over switch 44 as they are in spite of the heart beat signals supplied from the heart beat signal detector 50, and the heart beat synchronizing signal generator 48. The digital scanning convertor 24 makes these signals updated one after another so that the dynamic picture images obtained by the real-time sector scanning can be displayed at the display section 26. In this display mode the dynamic picture images are displayed at a fixed position in the television picture display screen. Incidentally, in I display mode it is also possible to supply only position signals of the ultrasonic beams by the electronic sector scanning in accordance with the following position signals.

$$X = S(t) \cos \phi(t)$$

$$Y = S(t) \sin \phi(t)$$

By such means the mode change-over switch 44 does not make the output invalid from the position signal generator 46 but only makes position signals invalid from the rotary encoders 36, 38 and 40 by means of supplying control signals to the position signal generator 46.

A II display mode is the mode which displays the still picture images in optional time phases in the real-time sector scanning. The instruction for still signals to the control panel of the mode change-over switch 44 by the examiner in an optional time phase, in requested time phase in diagnosis of moving organs in the above mentioned I display mode for example, causes one frame of electrionic sector picture image memorized and stored in the digital scanning convertor 24 as a still picture image and stops further memory update. According to this display mode, therefore, selected still picture images can be repeatedly displayed in the display section 26, and the picture images can be precisely observed in detail by the examiner. In this II display mode, when the optional time phase being instructed to the mode change-over switch 44 is controlled by the heart beat synchronizing signals supplied from the heart beat synchronizing signal generator 48, it is possible to observe a real-time still picture image made in optional time phase, systole or diastole for example, in the display section 26.

Figure 6:
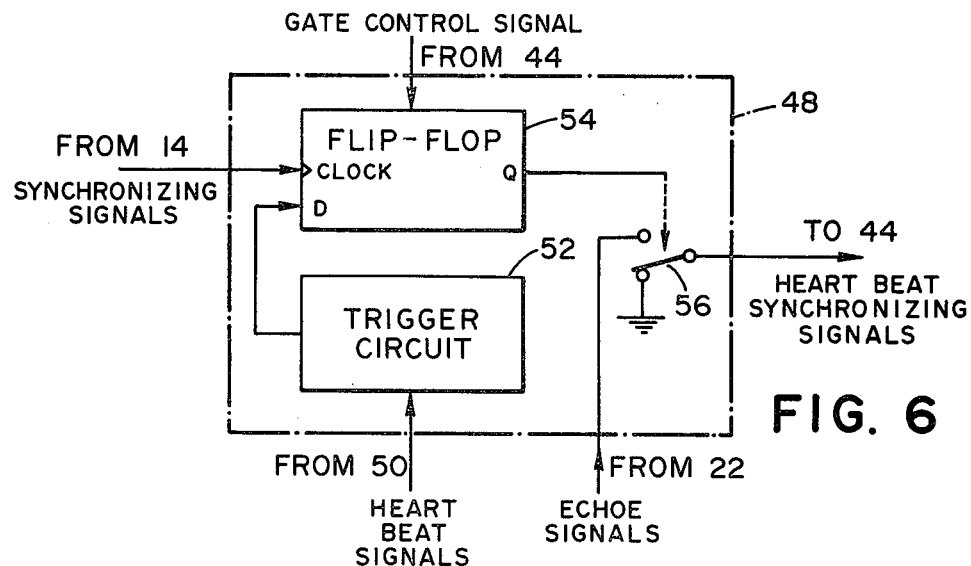
FIG. 6 is a block diagram showing one example of heart beat synchronizing signal generator in FIG. 2.
Figure 7:
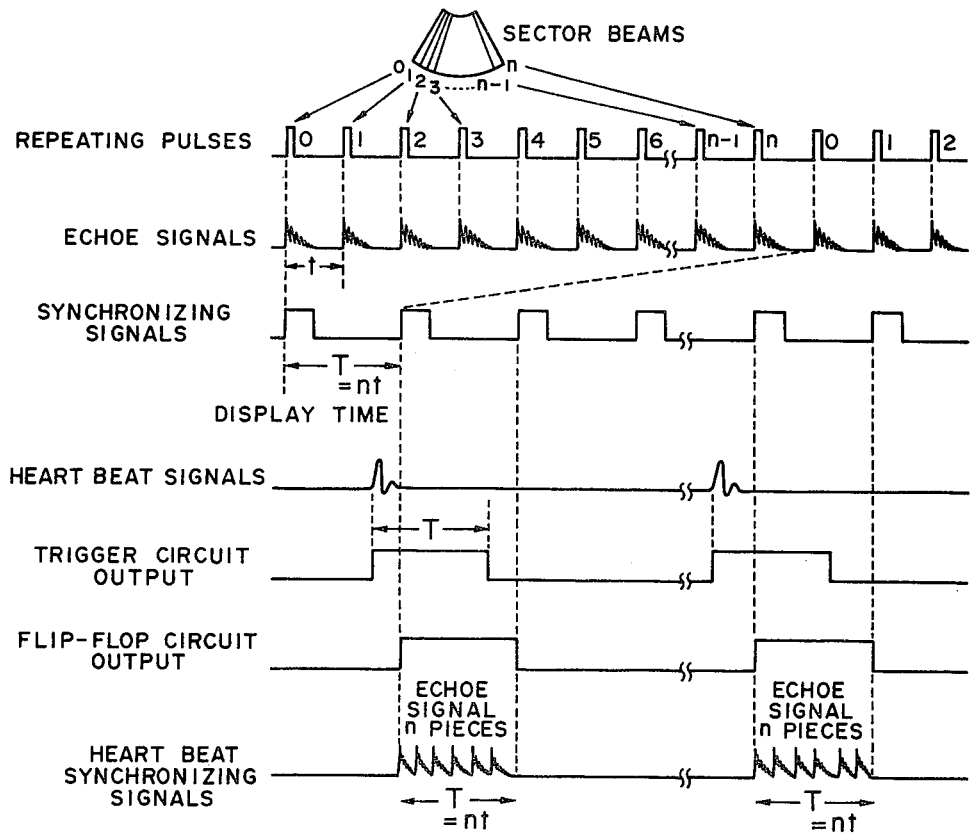
FIG. 7 is a wave form chart describing the action in FIG. 6.

In FIG. 6 shown therein is a preferred embodiment of the heart beat synchronizing signal generator 48, and its action is shown in the wave form chart in FIG. 7. The heart beat synchronizing signal generator 48 includes a trigger circuit 52 to which the heart beat signals of a heart beat signal detector 50 are supplied, a flip-flop 54, D input to which the output of the trigger circuit 52 is supplied and clock input of which sector one frame synchronizing signals of the repeating pulse generator 14 is provided and a switching circuit 56 which is controlled by the output from the flip-flop 54 to output or cut off the echo signals from the luminance modulation voltage generator 22.

In FIG. 7, the electronic sector scanning is performed by n times of ultrasonic sector beam transmitting and receiving, and each of transmitting and receiving cycles coincides with a repeating pulse t of the repeating pulse generator 14. At every transmitting and receiving action the illustrated echo signals can be obtained, and the dynamic picture images of the real-time sector scanning in the above described I display mode can be obtained when the memory storage in the digital scanning convertor 24 is updated one after another by the echo signals. The sector one frame synchronizing signals have cycles of $T = nt$, and it is evident that these cycles become sector scanning cycles. The heart beat signals are generated in optional time phase and these heart beat signals are detected by the trigger circuit 52. The output having a predetermined pulse period from the time of such detection is supplied from a one shot circuit prepared in the trigger circuit 52 to the D input of the flip-flop circuit 54. Accordingly, the flip-flop 54 is set by the sector one frame synchronizing signal after the trigger input is applied, and the selected echo signals during sector one frame period are supplied to the digital scanning convertor 24 so that the other echo signals are rejected by the off action of the switching circuit 56. The selected echo signals are updated at every heart beat signal generation, and still picture images synchronized to heart beat signals in real-time sector scanning can be continuously displayed at display section 26. These still picture images are held during one heart beat cycle and become the picture images which are updated at every heart beat period. Incidentally, it is also possible to obtain completely still picture images by means of activating the switching circuit 56 in on-state at one time being synchronized with the heart beat signals and holding the switching circuit 56 in off-state immediately. In FIGS. 6 and 7, the R wave of the heart beat signals is utilized for the input signal to the trigger circuit as it is, but it is also possible to obtain the still picture images of requested systole or diastole by means of delaying the R wave for a predetermined time.

A III mode is the mode which displays the dynamic picture images in compound sector scanning. The electronic sector scanning of the probe 10 is not only performed but also the compound scanning of the probe 10 is performed along the requested body surface over the organs to be diagnosed by the compound scanner 28. The combination of these two scanning methods causes a lot of picture image information be memorized in the digital scanning convertor 24, and the memorized and stored picture image information enables precise compound picture images to be displayed at the display section 26. The mode change-over switch 44 does not only put the heart beat synchronizing signal generator 48 in gate-on state continuously, but also reads the compound scanning position of the compound scanner 28 out of the position signal generator 46 so that the picture images on the television picture screen can be movably displayed. In other words, in accordance with the compound scanning of the probe 10 attached on the top end of the compound scanner 28, the position of the sector picture images within the display screen changes, but, at this time, it is possible to obtain the precise compound picture images as a whole since the input echo signals are stored as digital signals in the digital scanning convertor 24.

A IV display mode is the mode which displays the heart beat synchronizing still images in compound sector scanning. The picture image per sector one frame is stored from the different direction in the time phase which is synchronized with the heart beat signal in the position according with the compound scanning of the probe 10 so that the compound picture image can be obtained in the specific phase, systole or diastole for example. The heart beat synchronizing signals at this time are in the same manner as the above described in FIGS. 6 and 7.

In the embodiment, a UCG mode display is performed as a V display mode. In this case, the ultrasonic beams from the probe 10 are fixed to one direction by operation of the transmitting-receiving control circuit 12, and the timely change at this time is memorized in the digital scanning convertor 24 as UCG picture image signals. The mode change-over switch 44 makes the actions of the position signal generator 46 and the heart beat synchronizing signal generator 48 become invalid, and the UCG picture images can be displayed in the same manner as the prior art device.

As described heretofore, according to the present invention, the picture image signals obtained by the combination of the electronic sector scanning and the compound scanning can be displayed by the selected display modes, and a plurality of picture images in different kinds can be obtained so that the accurate diagnosis information can be obtained. Particularly, according to the present invention, it becomes possible to grasp heart conditions totally, and it is preferable to provide useful information for surgical operations.

What we claim is:

1. An ultrasonic compound scanning diagnostic apparatus comprising:
    an electronic sector scanning probe in which a plurality of ultrasonic transducers are arranged at equal distance from each other;
    a compound scanner holding the probe to perform free compound scanning along a selected body surface over the organs to be diagnosed;
    a plurality of rotary encoders coupled to said compound scanner to detect compound scanning positions of the probe;
    a transmitting and receiving control circuit which electronically scans the probe and transmits and receives sector scanning ultrasonic beams to and from a body to be examined;
    a digital scanning converter which memorizes and stores the echoe signals obtained from said transmitting-receiving control circuit and performs a selected signal conversion;
    a display section which displays picture images in accordance with picture image signals output from said digital scanning converter;
    a mode change-over switch which is connected to said digital scanning converter and switches to select a requested display mode by controlling memory storage and signal conversion of the echo signals in said digital scanning converter;
    a position signal generator which outputs picture image display position signals to said mode change-over switch in accordance with compound scanning position detecting signals obtained from the rotary encoders of said compound scanner; and
    a heart beat synchronizing signal generator which outputs heart beat synchronizing signals to said mode change-over switch in accordance with heat beat signals;
    whereby operation of said change-over switch makes it possible to display dynamic picture images or still picture images at optional time phases by real-time sector scanning and compound sector scanning.

2. An ultrasonic diagnostic apparatus according to claim 1, wherein said heart beat synchronizing signal generator comprises:
    a trigger circuit to which heart beat signals of a heart beat signal detector are supplied;
    a flip-flop having a D input to which the output of the trigger circuit is supplied and a clock input to which synchronizing signals of a repeating pulse generator is provided; and
    a switching circuit which is controlled by the output from the flip-flop to output or cut off the echo signals from the transmitting and receiving control circuit.

3. An ultrasonic diagnostic apparatus according to claim 2, wherein said display section comprises a television screen.

4. An ultrasonic diagnostic apparatus according to claim 3, wherein said heat beat synchronizing signal generator further comprises a means for selecting systole or diastole as the beat to be synchronized to.

5. An ultrasonic diagnostic apparatus according to claim 4, wherein said means for selecting systole or diastole comprises a gate circuit.

* * * * *